United States Patent [19]

Feldblum

[11] Patent Number: 5,724,995
[45] Date of Patent: Mar. 10, 1998

[54] METHOD FOR SCREENING FACTORS ON A PARALYSIS MODEL AND METHOD FOR OBTAINING THIS MODEL

[76] Inventor: Sophie Feldblum, 24 Avenue de Suffren, 75015 Paris, France

[21] Appl. No.: 558,887

[22] Filed: Nov. 16, 1995

[30] Foreign Application Priority Data

Nov. 21, 1994 [FR] France .................................. 94 13905

[51] Int. Cl.$^6$ .................................................. A61B 19/00
[52] U.S. Cl. .................................................. 128/898
[58] Field of Search .................................. 128/898

[56] References Cited

PUBLICATIONS

Kobrine et al., "Effect of intravenous lidocaine on experimental spinal cord injury," Journal of Neurosurgery, vol. 60, pp.595–601, Mar. 1984.
Cole et al., "Halothane, Fentanyl/Nitrous Oxide, and Spinal Lidocaine Protect Against Spinal Cord Injury in the Rat," Anesthesiology, vol. 70, pp. 967–972, Jun. 1989.
Cole et al., "The Effect of Fentanyl Anesthesis and Intrathecal Naloxone of Neurologic Outcome Following Spinal Cord Injury in the Rat," Anesthesiology, vol. 71, pp. 426–430, Sep. 1989.
Pointillart et al., "Effects of Nimodipine on Posttraumatic Spinal Cord Ischemia in Baboons," Journal of Neurotrauma, vol. 10(2), pp. 201–213, 1993.
T. Ueno, et al; The Annals of Thoracic Surgery; Jul. 1, 1994; vol. 58; No. 1; "Spinal Cord Protection: Development of a Parapalegia–Preventive Solution"; pp. 116–120.
H.H. De Haan, et al; Pediatric Research; Sep. 1993; vol. 34; No. 3; "Possible Neuroprotective Properties of Flunarizine Infused After Asphyxia in Fetal Lambs Are Not Explained by Effects on Cerebral Blook Flow or Systemic Blood Pressure", pp. 379–384.

D. Martin, et al; Journal of Neuroscience Research; Aug.1992; vol. 32; No. 4; "Experimental Acute Traumatic Injury of the Adult Rat Spinal Cord by a Subdural Inflatable Balloon Methodology, Behavioral Analysis and Histopathology"; pp. 539–550.

M. Tarloy, et al; Archives of Neurology and Psychiatry; 1953; vol. 70; "Spinal Cord Compression Studies" pp. 813–819.

C.H. Tator, et al; The Canadian Journal of Surgery; 1973; vol. 16, "Acute Spinal Cord Injury in Primates Produced by An Inflatable Extradural Cuff" pp. 222–231.

D. Martin, et al; "Brain Research Bulletin"; 1993; vol. 30; Syngeneic Grafting of Adult Rate DRG–Derived Schwann Cells to the Injured Spinal Cord; pp. 507–514.

*Primary Examiner*—John P. Lacyk
*Assistant Examiner*—Eric F. Winakur
*Attorney, Agent, or Firm*—Larson & Taylor

[57] ABSTRACT

The method makes it possible to induce in an animal a paralysis, preferably paraplegia, which is total and reversible in a predetermined period of time, with the aid of a balloon which compresses the spinal marrow. The animal model is employed in a method for testing candidate factors with neuroprotective and/or neuroregenerative function, which are considered as positive if a reduction in the duration of the paralysis can be observed. Medicinal products, in particular neuroprotective and/or neuroregenerative medicinal products, comprising an active principle demonstrated by the test method.

19 Claims, No Drawings

METHOD FOR SCREENING FACTORS ON A PARALYSIS MODEL AND METHOD FOR OBTAINING THIS MODEL

The present invention relates to a method for testing or screening factors with neuroprotective or regeneration function on an animal model of induced paralysis, preferably paraplegia. It also relates to the method making it possible to induce paralysis, in particular paraplegia, in the animal as well as to factors responding positively to the screening method.

In order to study the pathophysiology of compression lesions of the spinal marrow in humans and to make it possible to evaluate methods for therapy of these lesions, authors have for a very long time turned their attention to developing methods aimed at causing marrow lesions artificially, with the intention of inducing total and permanent paralysis or paraplegia in animals.

As early as 1953, I. M. TARLOV et al. (A.M.A. Archives of Neurology and Psychiatry, volume 70, pages 813–819) described a device making it possible to produce a gradual medullary compression in a conscious dog by fitting a balloon in the subdural space, the intensity of inflation of which balloon determined the degree of compression. The authors concluded simply that it is possible to obtain total paralysis.

The principle of balloon compression was readopted in 1973 by C. M. TATOR (The Canadian Journal of Surgery, Volume 16, pages 222 to 231) and applied to monkeys. The compression means is an annular balloon which is placed around the spinal marrow in the extra-dural space. Under the trial conditions, immediate total paraplegia (observed after 1 week) is obtained using 250 mmHg for 5 mins, followed by partial recovery observable from the fourth week onwards. In another trial, with the same degree of compression (350 mmHg) for 5 mins, on 10 paralysed monkeys, half remained paraplegic at the end of 12 weeks, whereas the other half exhibited only partial recovery from the fourth week onwards.

In 1992, D. MARTIN et al. (Journal of Neuroscience Research 32: 539 to 550) adapted the balloon compression model to rats by using GV15 balloons (Ingénor, Paris) inflated by fluid volumes ranging from 10 to 100 µl with the aid of a Hamilton syringe and using a catheter. The animals are anaesthetized by intraperitoneal injection of a mixture of xylazine and ketalar. After incision of the skin, the paravertebral muscles are detached and a laminectomy is carried out at T8, T9 or T10. The dura mater is opened and the balloon is introduced into the subarachnoid space and displaced rostrally to the extent of one or two vertebrae above the laminectomy. The degree of compression is, here again, essentially a function of the volume of liquid injected into a given balloon. Observations are made at intervals of one week. With a compression duration of 5 mins, the volume threshold was 40 µl for obtaining total and lasting paraplegia, which was the desired aim. With low degrees of compression, the authors merely observed a reduced and temporary motor deficiency (10 µl) on the Tarlov scale or a temporary paraparesis of variable magnitude (20 and 30 µl), with full motor recovery after 4 weeks (see also D. MARTIN et al., Brain Research Bulletin, volume 30, pages 507 to 514, 1993).

In contrast to the teaching of these documents, the inventor has unexpectedly and surprisingly discovered that it was possible to induce, very simply and perfectly reproducibly, total paraplegia of short duration, in particular of the order of approximately one week, in an animal such as a rat and that this method made it possible to develop an animal model for rapid screening of factors with a view to studying their potential as recovery promoters. This discovery can be extended to the induction of paralysis of short-duration quadriplegia type, as well as to the induction of paralysis, in particular paraplegia, of varied duration.

The invention makes it possible for the first time to screen factors on a model of paralysis, preferably paraplegia, which is total and reversible and which furthermore has standardized duration. The invention therefore relates to a method for testing or screening candidate factors with neuroprotective and/or neuroregenerative function, in which the candidate factor is administered to an animal having a paralysis which is total but reversible with predetermined duration, and the capacity of this substance to reduce the duration of the paralysis is detected. The method is particularly noteworthy in that it is the first so far to permit direct study of the action of a candidate factor on a natural recovery phase of paralysis, in particular paraplegia.

The term neuroprotective factors means, in particular, factors capable of limiting the initial lesion whereas neuroregenerative factors means, in particular, factors capable of stimulating axon regrowth and of thus facilitating restructuring of the injured region. These two types of factor can be grouped under the definition recovery promoters. The factors include chemical substances and cells or cells of a cell line which are capable of being grafted.

Preferably applied to animals, in particular rats, having paralysis, preferably paraplegia, which is total and of short duration, according to the invention the factor test method is noteworthy in that it is very fast; the preferred model is that of paraplegia which is reversible in an average of approximately 6 days (see the table in the Results section below). The end of paralysis, here paraplegia, is defined by partial motor recovery corresponding to the observation of the beginning of walking. If it is based on full motor recovery (normal walking and ability to stand up), this preferred model reaches the latter stage in an average of approximately 9 days.

According to the invention, the candidate factor may be administered to the animal before or after the compression and preferably a short time interval from this compression, which may, in particular, range from several minutes before compression to several minutes or hours after compression. The factor will preferably be administered approximately 1 hour after compression. In the case of factors with regenerative potency, it may be administered later, but generally not later than the 3rd to 5th post compression days. The factors are preferably administered by injection; the cells or cells from a cell line are grafted, in particular injected, at the compression site.

The invention relates in particular to a method for testing or screening such factors, in which a paralysis, preferably paraplegia, which is total but reversible with predetermined duration, in particular with an average of approximately 6 days, is induced in the animal, in particular a rat, by compression of the spinal marrow of the anaesthetized animal with the aid of a balloon, and in which, before, during or after compression, the factor to be tested is administered to the animal, then the capacity of this factor to reduce the duration of the paralysis, in particular paraplegia, is detected.

Induction of the reversible paralysis, in particular paraplegia, in the context of this test method is preferably carried out as described below with regard to the method intended to induce a paralysis, in particular paraplegia, according to the invention.

The present invention therefore also relates to the method making it possible to induce a total and naturally reversible paralysis, preferably paraplegia, in animals, in particular rats, comprising the steps of placing a balloon in contact with the spinal marrow, of inflating the balloon so as temporarily to compress the spinal marrow under conditions leading to the obtaining of a paralysis, preferably paraplegia, which is total and reversible with predetermined duration, then of deflating and withdrawing the balloon.

The balloon is preferably inserted into the subdural space. In order to obtain paraplegia according to the invention, the balloon may be inserted at the lower or upper thoracic level, preferably at the lower thoracic level, or at the lumbar level, in particular the lower lumbar level; insertion at the lower thoracic level ranging from T6 to T13, and for example at the T9–T10 level, will be preferred. The insertion may be carried out at the cervical level in order to obtain quadriplegia.

Use is preferably made of a balloon designed to induce paraplegia which is reversible in an average of approximately 6 days in animals anaesthetized by means of an anaesthetic having neuroprotective properties. According to the invention, the anaesthetics of this type are, in particular, chosen from the group consisting of ketamine (belonging to the family of dissociative bound anaesthetics), xylazine (a benzodiazepine) or a mixture thereof. A preferred anaesthetic is a mixture of ketamine and xylazine. Other suitable anaesthetics are indicated further on in connection with the animal used as model.

The standard balloon model for carrying out the invention is a balloon of Goldvalve GV15 type from Ingénor Paris which, at its maximum capacity, can contain a volume of 100 µl and has a length of 8 mm and a diameter of 6 mm.

In a preferred embodiment of the invention, the method for producing paraplegia which is reversible in an average of approximately 6 days (see the table in the Results section below) comprises the injection into the balloon of a volume of approximately 10 µl, on animals anaesthetized by means of an anaesthetic as described above.

This type of anaesthetic has the property of shortening the motor recovery time. Using an anaesthetic without neuroprotective property, such as the anaesthetic equithezine, leads, under the same volume conditions, to a recovery time which is longer but remains within the context of the invention, in particular 10 days on average for partial motor recovery (see the table in the Results section) and approximately 16 days on average for full motor recovery.

It is also possible to vary the duration of the paraplegia or of the quadriplegia by modifying the volume injected into the balloon. The invention also relates to the use of inflation volumes which are close to the said 10 µl while remaining preferably below 20 µl.

It is clear that, on the basis of the standard balloon model indicated and the conditions in which it is used, it is within the capacity of the specialist to select and try other balloons and to determine for them, for example by trials, those parameters which are suitable without departing from the context of the invention.

Particular models of paraplegia which is reversible in approximately 6 and 10 days have been presented above. It is clearly obvious that the invention permits the person skilled in the art to create models of paraplegia or quadriplegia having different durations, in particular by altering the characteristics of the balloons and the volume injected.

The balloon is preferably placed medially relative to the spinal marrow, in order to obtain a bilateral paralysis, in particular paraplegia. However, the invention also makes it possible to produce unilateral paralysis by placing the balloon laterally relative to the spinal marrow. An animal which retains unilateral motor function is thus obtained.

Finally, although the animal model described in detail here is the rat, the invention also covers the use of other animals such as, in particular, cats, dogs and monkeys. The operating conditions can be adapted to the selected animal with the aid of trials based on the principles established in this application. Useable anaesthetics are indicated further on for each animal.

The invention also relates to:

any neuroprotective and/or neuroregenerative medicinal product whose active principle has been demonstrated by the test method; these active principles may equally well comprise chemical substances or cells or cells from a cell line;

medicinal products comprising substances, molecules, cells or cells from a cell line which have never been used by way of medicinal product and respond positively to the test method;

the use of substances, molecules, cells or cells from a cell line which are known in therapeutics and respond positively to the test, for the preparation of neuroprotective medicinal and/or neuroregenerative products.

In addition to the active principle, these medicinal products may comprise, as is common practice, acceptable pharmaceutical excipients.

The invention will now be described in more detail below, in particular by indicating, by way of non-limiting example, a way of inducing paraplegias which are reversible with average durations of 6 and 10 days, respectively.

Equipment used:

The medullary lesion is produced using an inflatable balloon initially intended for the occlusion of intracranial vascular malformations (Goldvalve GV15 balloon, Ingénor, Paris). At its maximum capacity, the balloon can contain a volume of 100 µl and has a length of 8 mm and a diameter of 6 mm. With a view to implanting the balloon in the subdural space, the latter is connected via a polyethylene catheter of external diameter 0.96 mm (Biotrol) itself connected to a base (BALT) connected to a 3-way tap which is itself connected to a 1 ml syringe.

For each new balloon, a calibration can be made by inflating the balloon with the aid of a Hamilton syringe with a capacity of 50 µl. Impressions of the size of the balloon with inflations of 10, 20, 30, 40 and 50 µl are obtained by photography and are compared with the impressions of the reference balloon previously used. In case of divergence, the calibration parameter is the inflation volume which can therefore vary slightly around 10 µl for this type of balloon.

Method:

The balloon is implanted and inflated in animals (Sprague-Dawley female rats, Iffa Credo) anaesthetized by an intramuscular injection of a mixture of xylazine (15 mg/kg) (Rompun) and ketamine (100 mg/kg) (Imalgene) or else Equithesine. After opening of the skin, the paravertebral muscles are retracted from the posterior arches of the vertebrae. A laminectomy of a vertebra at the T9–T10 thoracic level is carried out in order to lay bare the spinal marrow. The dura mater is opened with the aid of a 25 G needle. The deflated balloon is then inserted through this orifice, rostrally with respect to the laminectomy. The balloon is inflated under intact laminae. The duration and the degree of compression can be altered according to the type of severity desired. In order to obtain total paraplegia which is fully reversible in an average of approximately 9 days (full motor recovery), an inflation corresponding to an injection of 10 µl of distilled water over 5 minutes was carried out.

The balloon is next deflated then withdrawn and the wound is sutured. The animals are then placed in individual cages in a thermostatted environment (28° to 30° C.) and are fed ad libitum.

Result:

The method which has just been described was applied to two groups of rats, each group receiving one of the two anaesthetics indicated. The induction of total paraplegia on awakening of the animals was observed in 100% of cases. In the animals treated with the xylazine/ketamine mixture, daily observation of these animals demonstrated that this paraplegic state lasts on average 6 days before it is possible to observe poorly coordinated movements of the posterior limbs and the beginning of walking. It is necessary to wait approximately 3 more days still for these animals to regain normal walking and the faculty of standing up. This full recovery of motor function was observed in 100% of cases. In addition to this behavioural reproducibility, post-mortem macroscopic analysis of the marrow of these animals showed, at the compression site, a lesion extending on average over 1 cm. This lesion is characterized by a depression corresponding to the point of impact of the balloon and by opacity of the tissue. Microscopic analysis demonstrated the presence of a cavity with destruction of the white and grey substance, as well as an astrocyte gliosis, characterized by the immunodetection of glial fibrillary acidic protein (GFAB), a specific marker of astrocytes. Thus, in spite of full motor recovery, a significant tissue lesion persists.

TABLE

| Anaesthetic | Equithesine | Ketamine/ Xylazine |
| --- | --- | --- |
| Sample size: | 17 | 19 |
| Average paraplegia duration*: | 10.059 | 5.8947 |
| Standard deviation: | 5.8145 | 3.9143 |
| Standard error: | 1.4102 | 0.8980 |

*based on the observation of beginning of walking = partial motor recovery.
The statistical test is a Mann-Whitney test:
- cut-off value: 81.500
- P = 0.0117; this value, less than 0.05, is considered as significant.

Acceleration of the motor recovery:

On the basis of this animal model in which the paraplegia persists for approximately one week, it is possible to search for factors which can interact positively with this paraplegia period and shorten it, in order to propose candidates for inducing the recovery of motor function in paraplegic humans. This rapid screening test for recovery-promoter products is particularly useful before proceeding to the subsequent stage of application in humans. Recovery promoters include neuroprotectors whose role is to limit the initial lesion, and also neuroregenerators which can stimulate axon regrowth and thus facilitate restructuring of the injured region.

Depending on the lesion step in question, there are various classes of neuroprotectors, including anti-ischemics, glutamate antagonists, calcium antagonists and free-radical antagonists. Mention may, in particular, be made of non-competitive antagonists of N-methyl-D-aspartate (NMDA) which are capable of preventing glutamate toxicity. Mention may further be made of free-radical inhibitors such as lazaroid derivatives.

Among neuroregenerators there are also various classes of molecules depending on whether axon growth promotion or glial scar reduction is targeted.

The new factors can be tested in accordance with the method according to the invention. In the case of factors responding positively to the test, their neuroprotective or neuroregenerative activity can then be determined, in particular by histological examination.

The method preferably provides for the use of groups of rats which are subjected to medullary compression and to which the factor to be tested is administered. The impact of this factor on the duration of the paraplegia is determined by the shift in the average of the paraplegia durations (until partial or full motor recovery) of the rats in the group, compared to a predetermined standard average (for example 6 days) or compared to a treated control group having undergone medullary compression in parallel.

The animals in the test groups and in the control groups will in general be sacrificed, in particular to carry out the necessary histological examinations. In the absence of an examination requiring sacrifice of the animal, the persistence of a significant lesion at the compression site also leads to sacrifice of the animal being selected.

Anaesthetics:

Neuroprotective anaesthetics are indicated below, by way of non-limiting examples, in connection with the animal intended to be used as a model according to the invention. The person skilled in the art is perfectly well aware of these anaesthetics and of their mode of use.

| | |
| --- | --- |
| I - CAT: | Atropine |
| | Xylazine |
| | Central analgesics |
| | Myorelaxants |
| | Ketamine |
| | Midatrene |
| II - DOG: | Atropine |
| | Neuroleptics |
| | Benzodiazepines |
| | Barbiturates |
| | Neuroleptanalgesia |
| III - MONKEY: | Atropine |
| | Acepromazine |
| | Ketamine |
| | Xylazine |
| | Alfadione |

I claim:

1. Method for testing a candidate factor with neuroprotective and/or neuroregenerative function, which comprises:
   administering a candidate factor with neuroprotective and/or neuroregenerative function to an animal having a paralysis which is total but reversible with predetermined duration, and
   determining the capacity of the candidate factor to reduce the duration of the paralysis.

2. Method according to claim 1, wherein the paralysis is a paraplegia.

3. Method according to claim 2, wherein the animal is a rat having paraplegia which is reversible in an average of approximately six days.

4. Method for testing a candidate factor with neuroprotective and/or neuroregenerative function, which comprises:
   applying to an anesthetized animal a compression of its spinal marrow with the aid of a balloon to induce in the animal a paralysis which is total but reversible with predetermined duration,
   administering to the animal in which said paralysis has been induced a candidate factor with neuroregenerative and/or neuroregenerative functions, and
   determining the capacity of the candidate factor to reduce the duration of the paralysis.

5. Method according to claim 4, wherein the paralysis is a paraplegia.

6. Method according to claim 5, wherein the anaesthetized animal is an anesthetized rat having paraplegia which is reversible in an average of approximately six days.

7. Method according to claim 4, wherein the balloon is a Goldvalve GV15 type inflated with approximately 10 µl of a liquid.

8. Method according to claim 7, wherein the balloon is inflated for approximately five minutes.

9. Method according to claim 4, wherein to induce the spinal compression, the balloon is inserted into the subdural space of the animal at its lower thoracic level.

10. Method according to claim 9, wherein the balloon is inserted at the T9–T10 level.

11. Method according to claim 4, wherein the spinal compression is conducted on an animal which is anesthetized by means of an anesthetic having neuroprotective properties.

12. Method according to claim 4, wherein the spinal compression is conducted on an animal which is anesthetized by means of an anesthetic having no neuroprotective properties.

13. Method for inducing in an animal a paralysis which is total and reversible, comprising the steps of placing a balloon in contact with the spinal marrow of said animal, inflating the balloon so placed to temporarily compress the spinal marrow under conditions leading to the obtaining of a paralysis which is permanent and reversible in a predetermined duration, and then deflating and withdrawing the balloon.

14. Method according to claim 13, wherein the animal is a rat.

15. Method according to claim 14, wherein the paralysis is paraplegia.

16. Method according to claim 13, wherein the balloon is inserted into the subdural space of the animal at its lower thoracic level.

17. Method according to claim 16, wherein the balloon is inserted at the T9–T10 level.

18. Method according to claim 13, wherein the spinal compression is conducted on an animal which is anesthetized by means of an anesthetic having neuroprotective properties.

19. Method according to claim 13, wherein the spinal compression is conducted on an animal which is anesthetized by means of an anesthetic having no neuroprotective properties.

* * * * *